United States Patent
Rapoport et al.

(10) Patent No.: US 10,208,281 B2
(45) Date of Patent: Feb. 19, 2019

(54) METHOD FOR CULTIVATING CELLS IN ADHESION CULTURE BY USING A CELL CULTURE CARRIER IN CAPSULE FORM, AND CELL CULTURE CARRIER THEREFOR

(71) Applicant: Fraunhofer-Gesellschaft zur Foerderung der angewandten Forschung e. V., Munich (DE)

(72) Inventors: Daniel Hans Rapoport, Luebeck (DE); Miriam Voigt, Bad Schwartau (DE); Charlotte Walter, Luebeck (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/033,108

(22) PCT Filed: Sep. 22, 2014

(86) PCT No.: PCT/EP2014/002567
§ 371 (c)(1),
(2) Date: Apr. 28, 2016

(87) PCT Pub. No.: WO2015/062686
PCT Pub. Date: May 7, 2015

(65) Prior Publication Data
US 2016/0264931 A1  Sep. 15, 2016

(30) Foreign Application Priority Data
Oct. 30, 2013 (DE) .................. 10 2013 018 242

(51) Int. Cl.
*C12M 1/12* (2006.01)
*C12N 5/00* (2006.01)

(52) U.S. Cl.
CPC ........... *C12N 5/0012* (2013.01); *C12M 25/01* (2013.01); *C12M 25/16* (2013.01); *C12N 2533/54* (2013.01); *C12N 2533/74* (2013.01); *C12N 2537/00* (2013.01); *C12N 2537/10* (2013.01)

(58) Field of Classification Search
None
See application file for complete search history.

(56) References Cited

FOREIGN PATENT DOCUMENTS

| WO | 2005121319 A1 | 12/2005 |
| WO | 2007146319 A2 | 12/2007 |

OTHER PUBLICATIONS

Karoubi et al., Biomterials, 2009, vol. 30, p. 5445-5455.*
Karoubi et al., Biomaterials, 2009, vol. 30, p. 5445-5455.*
Lima et al., Acta Biomater., 2012, vol. 8, No. 12, p. 4334-4341, published Online Aug. 3, 2012.*
Shi et al., Biotechnology & Bioengineering, 2005, vol. 92, No. 5, p. 643-651.*
Ashida et al. "Competing two enzymatic reactions realizing one-step preparation of cell-enclosing duplex microcapsules." Biotechnology Progress 29.6 (2013): 1528-1534.
Ehrhart et al. "Biocompatible coating of encapsulated cells using ionotropic gelation." PloS one 8.9 (2013): e73498.
Li et al. "Preparation of alginate-gelatin capsules and its properties." Frontiers of Materials Science in China 2.3 (2008): 253-260.
Liu et al. "Impact of the composition of alginate and gelatin derivatives in bioconjugated hydrogels on the fabrication of cell sheets and spherical tissues with living cell sheaths." Acta Biomaterialia 9.5 (2013): 6616-6623.
Liu et al. "Production of endothelial cell-enclosing alginate-based hydrogel fibers with a cell adhesive surface through simultaneous cross-linking by horseradish peroxidase-catalyzed reaction in a hydrodynamic spinning process." Journal of Bioscience and Bioengineering 114.3 (2012): 353-359.
Moon et al. "Morphology and metabolism of hepatocytes microencapsulated with acrylic terpolymer-alginate using gelatin and poly (vinyl alcohol) as extracellular matrices." Journal of Biomaterials Science, Polymer Edition 16.10 (2005): 1245-1259.
Poertner et al. "Bioreactor design for tissue engineering." Journal of Bioscience and Bioengineering 100.3 (2005): 235-245.

(Continued)

*Primary Examiner* — Kade Ariani
(74) *Attorney, Agent, or Firm* — Caesar Rivise, PC

(57) ABSTRACT

The invention relates to a method for cultivating cells in adhesion culture, comprising at least the following steps: a) dissolving or suspending a cross-linkable, biocompatible material having adhesion points for cells in a cell culture medium; b) suspending cells in the cell culture medium, which contains the cross-linkable, biocompatible material, or in a medium that contains at least one component that is required for the cross-linking of the cross-linkable, biocompatible material; c) introducing the cell suspension into a medium in drops under conditions that initiate or permit the cross-linking of the biocompatible material, wherein either the cell suspension or the medium into which the cell suspension is introduced in drops contains the cross-linkable biocompatible material; d) forming stable, preferably porous capsules from cross-linked biocompatible material, which capsules contain incorporated adherent cells; e) proliferating the adherent cells in the capsules for a specified time period; f) breaking up the capsule material by means of a physical or chemical stimulus and releasing the cells as a cell suspension. In an especially preferred embodiment of the invention, the method is performed cyclically, in that the cells released in step f) are suspended anew in a cell culture medium that contains a cross-linkable, biocompatible material or in a medium that contains at least one component that is required for the cross-linking of the cross-linkable, biocompatible material and steps c)-f) are repeated at least once.

19 Claims, 2 Drawing Sheets
(1 of 2 Drawing Sheet(s) Filed in Color)

(56) References Cited

OTHER PUBLICATIONS

Sakai et al. "Calcium alginate microcapsules with spherical liquid cores templated by gelatin microparticles for mass production of multicellular spheroids." Acta Biomaterialia 6.8 (2010): 3132-3137.
Warnock et al. "Bioreactor systems for the production of biopharmaceuticals from animal cells." Biotechnology and Applied Biochemistry 45.1 (2006): 1-12.
Yao et al. "Alginate and alginate/gelatin microspheres for human adipose-derived stem cell encapsulation and differentiation." Biofabrication 4.2 (2012): 025007.
International Search Report for PCT/EP2014/002567 dated Nov. 13, 2014.

* cited by examiner

METHOD FOR CULTIVATING CELLS IN ADHESION CULTURE BY USING A CELL CULTURE CARRIER IN CAPSULE FORM, AND CELL CULTURE CARRIER THEREFOR

BACKGROUND OF THE INVENTION

Efficient propagation of adherently growing cells still represents an unsolved problem, despite the fact that a number of different approaches have been pursued in this regard (for an overview, see e.g. Partner et al. in *Journal of Bioscience and Bioengineering*, Vol. 100, No. 3, 235-245, (2005) and Warnock et al. in *Biotechnol. Appl. Biochem.*, Vol. 45, 1-12 (2006)).

Propagation factors of only approx. $10^2$, in relation to a batch procedure, also referred to as "passage" in cell culture technology, can be achieved with the best technical devices (fixed bed reactors, hollow fiber reactors) at the current time. However, significantly higher factors of $10^3$ (e.g. for regenerative medicine and cell banks), $10^4$ (e.g. production cells for biomolecules) up to $10^6$ (e.g. for the food industry and agriculture) would be desirable.

This is precluded by the fact that adherent cells are only proliferative in a narrow density range. (Surface density approx. 500-50,000 cells/cm$^2$). Outside of this density range, the cells do not grow or they die off.

A surface which increases in size with the cell count could help to remedy this. The problems associated with this approach have, however, not yet been technically solved. This is due on one hand to the fact the increase in surface size would have to follow an exponential growth, and on the other hand that the technical possibilities to realize growing surfaces have hitherto been greatly restricted.

The best possibility at the current time lies in the use of microcarriers. These are particulate bodies (often spherically shaped, but a disc and rod shape are also possible) of typically approx. 1 mm in diameter, on the surface of which the cells can grow. Nutrient supply is performed by a medium in which the microcarriers are suspended. As soon as the cells have entirely grown over the carrier, they are detached (generally enzymatically) and seeded to new carriers. The growth surface also increases with the number of carriers.

This approach has a number of disadvantages. Firstly, the reactor size must be adjusted to the number of carriers; the volume ratio of the carriers to the total reaction volume must be within certain boundaries (generally 25-50%). As a result of this, the use of one and the same reactor to achieve high expansion factors is prohibited; instead, there must be progression from smaller to larger reactors. Secondly, a process technique is required at all times which can handle solid bodies (microcarriers) in a mechanically gentle manner, which is significantly more complex in terms of equipment than dealing with liquids. Liquids can be conveyed, filtered, sterilized, etc. much more easily. Thirdly, the volumetric use of the reactor is not very efficient because the cells can only grow on the surface of the carriers. Fourthly, the cells on the microcarriers are exposed to shearing and impact forces which are generated by convection of the medium and collision of the carriers. Fifthly, analysis of the cells on the microcarriers is difficult. In general, the cells on the carriers do not lend themselves well to analysis by microscope. Sixthly, the supply of cells generally exclusively occurs through the medium, which must be provided in a volume-filling manner and as free of gradient as possible. This results in inefficient utilization of the medium. Seventhly, the seeding of cells to the carriers (inoculation) and also the harvesting of the cells from the carriers represent technically difficult processes in which large proportions of the cells are lost.

Against this background, one object of the invention is to provide improved means and methods for efficient cultivation of cells in adhesion culture with which the described advantages of the prior art can be avoided or at least significantly reduced.

It was possible to achieve this object by the provision of the cultivation method as well as the provision of the cell culture carrier according to the invention.

DESCRIPTION OF THE INVENTION

The method according to the invention for cultivating cells in adhesion culture comprises at least the following steps:

a) dissolving or suspending a cross-linkable, biocompatible material with adhesion sites for cells in a cell culture medium, b) suspending cells in the cell culture medium which contains the cross-linkable, biocompatible material, or in a medium which contains at least one component which is required to cross-link the cross-linkable, biocompatible material, c) introducing the cell suspension into a medium in drops under conditions which initiate or allow the cross-linking of the biocompatible material, wherein either the cell suspension or the medium, into which the cell suspension is introduced in drops, contains the cross-linkable, biocompatible material, d) forming stable, preferably porous capsules of cross-linked, biocompatible material which contain incorporated, adherent cells, e) proliferating the adherent cells in the capsules for a defined time period, f) dissolving the capsule material by means of a physical or chemical stimulus and releasing the cells as a cell suspension.

In one preferred embodiment of this method, the cells released in step f) are once again suspended in a cell culture medium, which contains a cross-linkable, biocompatible material, or in a medium which contains at least one component which is required to cross-link the cross-linkable, biocompatible material, and steps c)-f) are repeated at least once. A significant increase in yield can thus be achieved in a simple and efficient manner.

The term "cross-linkable, biocompatible material", as used here, should firstly express that the relevant material is amenable to a polymerization, addition, condensation or other cross-linking reaction, which leads to a macromolecular product, preferably a hydrogel, and secondly that this material and the resultant macromolecular product is not substantially toxic for the cells.

In principle all cells which can be propagated in adhesion culture, more concretely, all cells which must grow in an adherent manner, can be considered as cells for cultivation in the cell culture carriers according to the invention. Specific, non-restricting examples of such cells comprise stem cells, somatic cells, primary cells, genetically modified cells (e.g. ips cells) and adherently growing production cell lines (e.g. CHO cells) as well as tumor cells, etc.

Proliferation of the cells in step e) typically occurs for a time period in the range from a few hours to 50 days, for example, 3-10 days. This time period is, however, not critical and it is also possible to deviate from this where desired, e.g. for specific types of cells. Step e) is usually carried out until the absorption capacity of the capsules is exhausted.

In one preferred embodiment of the method according to the invention, the conditions which initiate or allow the cross-linking of the biocompatible material in step c) encompass exposing the biocompatible material to a physical or chemical stimulus.

This physical or chemical stimulus in step c) is selected in particular from the group comprising a temperature change, pressure change, ultrasound, electromagnetic radiation, in particular visible light and UV, a pH change, the action of enzymes, radical starters, addition of water or exclusion of water, ions, in particular cations.

In more specific embodiments, the physical stimulus in step c) is, for example, an ultrasound treatment of the biocompatible material and the chemical stimulus in step c) is, for example, contact of the biocompatible material with a chemical agent, in particular selected from the group consisting of an enzyme, e.g. thrombin, and a bivalent cation, e.g. $Ca^{2+}$ or $Ba^{2+}$, or comprising the same.

In an even more specific embodiment of the method according to the invention, either a cell suspension, which contains alginate or alginate/gelatin as a cross-linkable, biocompatible material, is introduced in drops into a medium which contains a bivalent cation, e.g. $Ca^{2+}$ or $Ba^{2+}$, or a cell suspension in a medium, which contains a bivalent cation, e.g. $Ca^{2+}$ or $Ba^{2+}$, is introduced in drops into a medium which contains alginate or alginate/gelatin as a cross-linkable, biocompatible material. In the case of the latter method variant, small fluid spaces are generated which are surrounded by a gel membrane. The cells can also proliferate successfully in these spaces.

In further specific embodiments of the method according to the invention, the stimulus in step f) is selected from the group comprising a temperature change, pressure change, ultrasound, electromagnetic radiation, in particular visible light and UV, a pH change, the action of enzymes, in particular proteases and sucroclastic enzymes, complexing agents or solvents, or combinations thereof.

Even more specifically, the stimulus in step f) represents the action of proteases which are produced by the adherent cells themselves or comprises such an action.

In one preferred embodiment of the invention, the capsule material is porous. The pores typically have a size in the range from 50 to 3000 μm, preferably in the range from 100 to 1000 μm.

In one embodiment of the method according to the invention, step c) is therefore carried out under conditions which support pore formation in the capsule material.

This can occur, for example, in that a gas, for example, air, is injected into the medium into which the cell suspension is introduced in drops. During or after successful formation of the capsule material, typically a gel, the gas slowly escapes again and thereby generates pores.

In a different variant, a gas-forming particulate material, e.g. a carbonate, which releases gas after exposure to a physical or chemical stimulus, e.g. acid, preferably a mild acid such as acetic acid, etc., is enclosed in the capsule material. The particulate material is typically added in the form of an insoluble fine powder (particle size in the range of a few micrometers, e.g. 1-500, 1-100, 1-50 or 1-10 μm).

In one embodiment, the method according to the invention is characterized in that the cross-linkable, biocompatible material represents or comprises a material which can form a hydrogel.

This hydrogel can be a hydrogel based on natural substances, e.g. a protein-based hydrogel, a sugar-based hydrogel, containing modified oligo- or polysaccharides, or a synthetic hydrogel on the basis of polyesters, polyethers or polyalcohols.

In one preferred embodiment of the method according to the invention, the cross-linkable, biocompatible material is provided with adhesion sites for cells by a chemical coupling reaction.

These adhesion sites for cells can represent or comprise, for example, specific or non-specific adhesion or binding motifs for biological cells, e.g. amino groups, RGD peptides, RAD peptides or analogues thereof.

In more specific embodiments of the method according to the invention, the capsules composed of cross-linked, biocompatible material comprise a thermoresponsive material, e.g. poly-NIPAM or poly(hydroxypropyl)cellulose, a polyester, polyether or polyalcohol, silk, fibrin or cross-linked alginate.

Silk can be cross-linked by ultrasound (conformation change, formation of semi-crystalline regions, exclusion of water).

Fibrin is generated by cross-linking fibrinogen with thrombin/calcium. The fibrinogen is split proteolytically and converted into an active monomer which can react with further monomers and thus forms the fibrin gel.

Alginate and hydrogels derived from it can be formed by cross-linking with bivalent ions, in particular $Ca^{2+}$ or $Ba^{2+}$.

Polyesters can be formed by setting an expedient (acid, but tolerable in terms of cell physiology) pH value from the monomers; in principle, both synthetic and natural polyesters can be used.

Polyalcohols or polyols can be produced by transesterification of glycerin fats. If the reaction conditions used here are not tolerable in terms of cell physiology, the finished polymers can also be used, particularly in the form of switchable block polymers. These can react to temperature or pH differences with the exclusion of water and cross-link in this manner. The same applies to poly-NIPAM and polyhydroxypropyl cellulose.

In an even more specific embodiment, the method is characterized in that gelatin molecules are linked to an alginate framework structure, preferably by means of a carbodiimide coupling reaction, and the cross-linking of this alginate-gelatin precursor materials is carried out by contacting with a bivalent cation, in particular $Ca^{2+}$ or $Ba^{2+}$.

The origin and molar mass of the gelatins used is not critical. Both gelatin which was produced with an acid hydrolysis method and gelatin with an alkaline production method can be used.

The molar mass can in principle vary in a wide range from, for example, 1000 to 100,000 g/mol. A suitable molar mass can lie e.g. in a typical range for commercial gelatin varieties, i.e. approximately 50,000-80,000 g/mol.

However, a gelatin hydrolysate with a significantly smaller molar mass, e.g. approx. 1000-10,000, more specifically 3000 to 5000 g/mol, can also be expediently used. Gelatin with such smaller molar masses can be obtained, for example, by further enzymatic breakdown of commercial products.

The advantage of these products with a smaller molar mass lies in the fact that they can be dissolved in a higher monomer concentration without acting in a gelling manner and preventing/impairing the coupling reaction. In the case of gelatin with a molar mass of e.g. approximately 50,000-80,000 g/mol, in particular in the upper range, the viscosity can become so high with concentrations from approximately 1% in the reaction medium and at low temperatures that stirring is rendered very difficult.

Several non-restricting examples of suitable commercial gelatin varieties are listed below. The gelatin is characterized by its gelling force which is measured in bloom. The unit bloom indicates the mass of a die which can press a standardized impression into the gelatin.

a) Gelatin type A (acid method), 225 Bloom, Hahn
b) Gelatin type A, 300 Bloom, pig skin, Sigma
c) Gelatin type A, 90-110 Bloom, pig skin, Sigma
d) Gelatin type B (alkaline method), pig skin, Sigma The origin and molar mass of the alginate used is not especially restricted. In one specific embodiment, sodium alginate from brown algae (procured from the firm BioReagent in the degree of purity "Cell culture tested", i.e. sufficiently toxin-free and sterile) was used. The alginate used had "low viscosity", was therefore in the lower molar mass range between 50,000 and 80,000 g/mol.

In one preferred embodiment of the method according to the invention, the capsules composed of cross-linked, biocompatible material further contain immobilized nutrients and/or growth hormones. In this manner, the growth of the cells can be supported very efficiently with relative small amounts of active ingredients.

In one particularly preferred embodiment of the method according to the invention, the capsules composed of cross-linked, biocompatible material further contain immobilized reporter molecules. For example, the growth conditions or cell growth itself can be monitored with the aid of such reporter molecules.

In principle, all reporter molecules known in the prior art, in particular for similar purposes, can be contemplated as the reporter molecules.

The reporter molecules are typically dyes or fluorescence markers. Several non-restricting examples include fluorescein derivatives (e.g. 2",7"-bis-(2-carboxyethyl)-5-(and 6-)carboxyfluorescein (BCECF)), fluorecin derivatives, benzoxanthene derivatives, ruthenium complexes, etc.

In more specific embodiments, the reporter molecules are viscosity-sensitive, pH-sensitive, $CO_2$- or $O_2$-sensitive.

The reporter molecules can, among other things, display a change of at least one parameter in the capsule, e.g. a pH change or a change in the oxygen partial pressure, by a corresponding verifiable change in properties of the reporter molecules in the capsule, e.g. a color change, a change in fluorescence emission or absorption wavelength, a change in fluorescence lifetime.

Verifying the change of the parameter is typically carried out by a spectroscopic or spectrometric method, in particular selected from the group of VIS spectroscopy, fluorescence spectroscopy, time-resolved fluorescence spectroscopy, FRET spectroscopy, etc.

Verifying pH changes can be carried out directly by fluorescence measurements. Known fluorophores, for measuring the pH, include fluorescein and derivatives, or HTPS (8-hydroxypyrene-1,3,6,-trisulfonic acid). The absorption and emission wavelength are shifted in this case, which leads to an increase or reduction in the emitted intensity in the case of fixed stimulation/emission wavelengths.

In the case of $O_2$ measurement, one can make use of the effect that dissolved oxygen quenches the fluorescence of dyes, i.e. considerably reduces the lifetime of the stimulated state. As a result, one does not measure the average intensity here (as in the case of pH), rather the reduction in fluorescence after a short period of stimulation (stimulation blitz) in a time-resolved manner. Ru complexes (e.g. ruthenium(II) (4,7-diphenyl-1,10-phenanthroline)3) are well suited. In this case, the ligands would be bonded to the polymer matrix and the Ru salt would be added to this.

$CO_2$ sensors operate according to the same principle with the difference that the fluorescence lifetime is generally measured indirectly via a fluorescence transfer (FRET). Use is made here of the fact that the emitted radiation can only be absorbed by a different (nearby) fluorophore if the lifetime of the first fluorophore (generally again Ru-porphyrin complexes) is sufficiently long. The fluorescence intensity of the second fluorophore is then measured.

Impact quenching of a stimulated state (Stern-Vollmer equation) is also used for viscosity measurement. In principle, any fluorophore of which the initial decay time of the fluorescence is measured (in the nsec range) can be used for this purpose. For example, the degradation rate of the capsules can be verified or tracked by viscosity measurements.

A closely related aspect of the invention relates to the cell culture carrier used and produced in the above method in capsule form.

This cell culture carrier comprises a cross-linked, biocompatible material in capsule form which has adherent cells incorporated therein, and is characterized in that the cross-linked, biocompatible capsule material is dissolved by a physical or chemical stimulus and the cells can be released as a result of this.

More specifically, the cell culture carrier according to the invention is characterized in that the capsules can be dissolved by a stimulus which is selected from the group comprising a temperature change, pressure change, ultrasound, electromagnetic radiation, in particular visible light and UV, a pH change, the action of enzymes, in particular proteases and sucroclastic enzymes, complexing agents or solvents, or combinations thereof.

The cross-linked, biocompatible material of the cell culture carrier is preferably a hydrogel.

In specific embodiments, the capsules composed of cross-linked, biocompatible material comprise a thermoresponsive material, e.g. poly-NIPAM or poly(hydroxypropyl)cellulose, a polyester, polyether or polyalcohol, silk, fibrin or cross-linked alginate.

More specifically, the cell culture carrier is characterized in that the cross-linked alginate comprises an alginate framework structure with coupled-on gelatin molecules, preferably an alginate framework structure, in the case of which every second to thirtieth, preferably every fifth to fifteenth, particularly preferably approximately every tenth sugar molecule is provided with a gelatin protein side chain.

The size of the capsules is not especially restricted. The capsules generally have a size in the range from 0.1 mm to 40 mm, typically 3 to 5 mm.

In one preferred embodiment, the capsules composed of cross-linked, biocompatible material further contain immobilized nutrients and/or growth hormones.

In one particularly preferred embodiment of the invention, the capsules composed of cross-linked, biocompatible material further comprise immobilized reporter molecules as described above. These reporter molecules can be, for example, viscosity-sensitive, pH-sensitive, $CO_2$- or $O_2$-sensitive.

In one specific embodiment, the reporter molecules are dyes or fluorescence markers.

The use of the capsule-shaped cell culture carriers according to the invention with incorporated reporter molecules allows, for example, verification of a change of at least one reaction parameter in the capsule, e.g. a pH change or a change in the oxygen partial pressure, by a corresponding verifiable change in properties of the reporter molecules, e.g. a color change, a change in fluorescence emission or absorption wavelength, a change in fluorescence lifetime.

Verifying the change of the reaction parameter can, for example, be carried out by a spectroscopic or spectrometric method, in particular selected from the group of VIS spectroscopy, fluorescence spectroscopy, time-resolved fluorescence spectroscopy, FRET spectroscopy, etc.

The cell culture carrier according to the invention is suitable for a plurality of applications, for example, preparative cell culture techniques, including bioreactors to obtain certain biomolecules, and analytical cell culture techniques, e.g. in medical and pharmaceutical analysis.

A further aspect of the present invention correspondingly relates to a device which comprises a cell culture carrier as described above.

Such a device is in particular a reactor for the cell culture or a device for analysis.

Advantages of the Invention

Firstly, the reactor can also already be operated in its end size (target cell count) for very small initial cell counts. Due to the fact that the cells are enclosed in a local microenvironment, the reactor volume as such has less significance and the cells can communicate with one another locally via cytokines/growth factors, etc. without the concentration of these substances in the reactor having to homogeneously present.

Secondly, only fluids and suspensions are handled in the entire propagation process. Only conventional pump and filter systems are required. Conveying and processing of solid bodies are omitted entirely.

Thirdly, the cells do not grow solely on the surface of the capsules, but rather in the majority inside them. As a result, the reactor volume is used significantly more efficiently with high volume occupancy.

Fourthly, the cells inside the capsules are protected in a largely mechanical fashion. Shearing and impacts forces, as unavoidably occur during circulation of the medium, can cause a lot less damage than in a conventional carrier culture. Higher flow speeds and/or volume flows are simultaneously possible.

Fifthly, observation/analysis of the cells in the capsule is easier than on microcarriers. The capsules are generally transparent and are comparatively amenable to microscope analysis. At the same time, it is possible, as described above, to immobilize and optically read probe or reporter molecules in the gel of the capsules. Examples of such molecules are pH-dependent fluorescence dyes or dyes in the case of which the lifetime of the stimulated state is dependent on the oxygen concentration ($pO_2$ measurement by fluorescence quenching). Such reporter molecules can be easily optically read and directly display the state of supply of the encapsulated cells.

Sixthly, the capsule itself can contain nutrients and growth hormones (e.g. immobilized) so that it is possible to operate with a comparatively lean medium. The medium can be used significantly more efficiently by the local provision of the nutrients/growth hormones.

Seventhly, the conventional steps of inoculation/cell harvesting are omitted entirely and are replaced by the processes of encapsulation and capsule-dissolving. This enables much more simple and gentle introduction/removal of the cells into the reactor and out of it and enables handling of the cells with a reduced level of loss.

BRIEF DESCRIPTION OF THE FIGURES

The patent or application file contains at least one drawing executed in color. Copies of this patent or patent application publication with color drawing(s) will be provided by the Office upon request and payment of the necessary fee.

The following exemplary embodiment serves to further explain the invention, without restricting the same, however, to the specific parameters and conditions of the examples.

EXAMPLE 1

Cultivation of Cells in Alginate-Gelatin Capsules

The capsule material was produced by covalent chemical coupling of alginate with gelatin. Here, the alginate forms the actual hydrogel framework (backbone) to which binding sites for the cells are added by the gelatin. Cells cannot adhere/proliferate in pure alginate capsules. Adherently growing cells also do not propagate in physical alginate/gelatin mixtures. A chemical coupling is thus necessary.

The coupling reaction was carried out by means of carbodiimide:

In one approach, 40 mg sodium alginate was dissolved in 5 ml MES buffer (0.2 M, MES, 0.3 M NaCl, pH=6.5) at room temperature while stirring for approx. 30 minutes. At the same time, 1.2 g gelatin (Solugel P/400 from PB Gelatins GmbH, approx. 3 kDa mean molar mass; this involves gelatin hydrolysate (i.e. smaller gelatin fragments)) was dissolved in 15 ml MES buffer at 37° C. and 200 rpm for approx. 1 h. Briefly before the start of reaction, 6.7 μl (0.04 mmol) N-(3-dimethylaminopropyl)-N-ethylcarbodiimide (EDC) was provided in 10 ml MES buffer and 4.5 mg (0.02 mmol) N-hydroxysuccinimide sodium salt (Sulfo-NHS) was added. At 0° C., the alginate dissolved in MES buffer was subsequently added to the solution and the mixture stirred for 5 min. Thereafter, the gelatin was added to the reaction solution and the mixture stirred for 2 h at room temperature.

Purification was carried out by means of dialysis with distilled water for approx. 5 days. The material can be freeze-dried for storage.

The synthesized material was dissolved in cell culture and processed into capsules by introduction in drops into a solution containing $Ca^{2+}$. Cells previously suspended in the cell culture medium are then immobilized in the capsules and can grow adherently in them. Once the capsules have fully grown (depending on the type of cell and seeding density approx. 5-20 days), the capsule material was dissolved by addition of citrate or EDTA and the cells released.

The released cells are in suspension and the gelling agent can be added therein again and encapsulation can be performed. This cycle can be repeated as often as desired. The propagation factor for each cycle is approximately 10. A propagation by the factor $10^4$ therefore only requires the cycle to be repeated 4-5 times.

Figure 1:
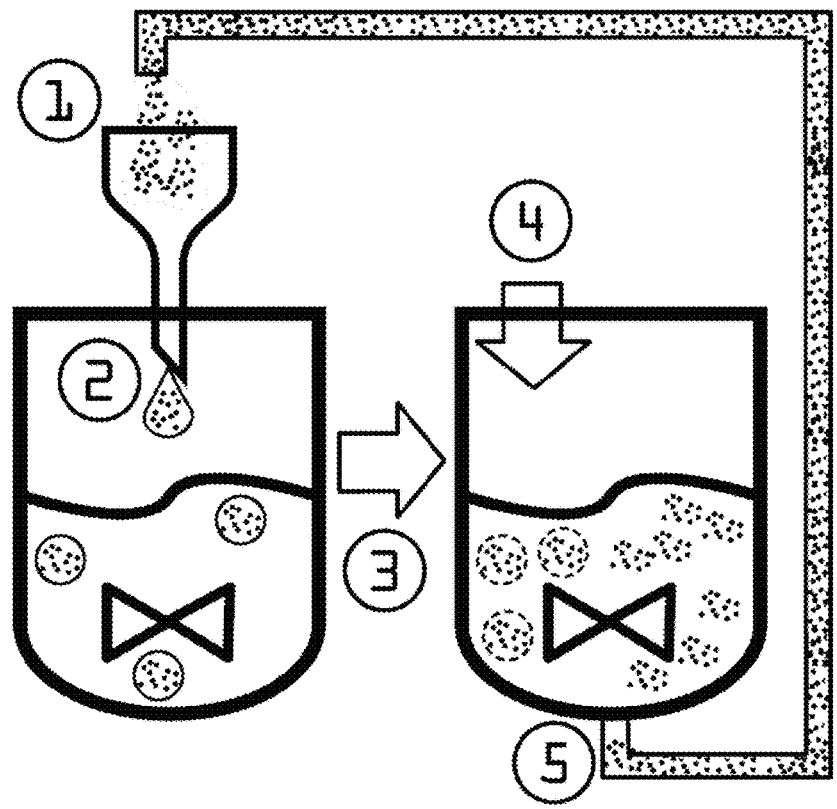
FIG. 1 schematically shows the main steps of the cultivation method according to the invention using a cell culture carrier in capsule form. 1: Suspending cells in a medium; 2: Introducing the cell suspension in drops and capsule formation; 3: Expansion phase; 4. Dissolving the capsules; 5: Transferring the released cells into the next cycle

The main steps described above can be summarized on the basis of the diagram shown in FIG. 1 in a generalized form. Step (1): Cells are suspended in a medium which also contains non-cross-linked hydrogel matrix (typically 1-4% m/v); Step (2): The suspension is introduced in drops into a gelling medium and forms stable capsules here in which cells can grow; Step (3): During the expansion phase, the capsule suspension is stirred or medium is replaced, etc.; Step 4: As soon as the cells in the capsules are confluent (optional readout by dyes), the capsules are dissolved by an external stimulus (e.g. addition of complexing agents, pH change, temperature change, etc.); Step (5): The released cells settle and medium and non-cross-linked matrix can be added for a next cycle.

Figure 2:
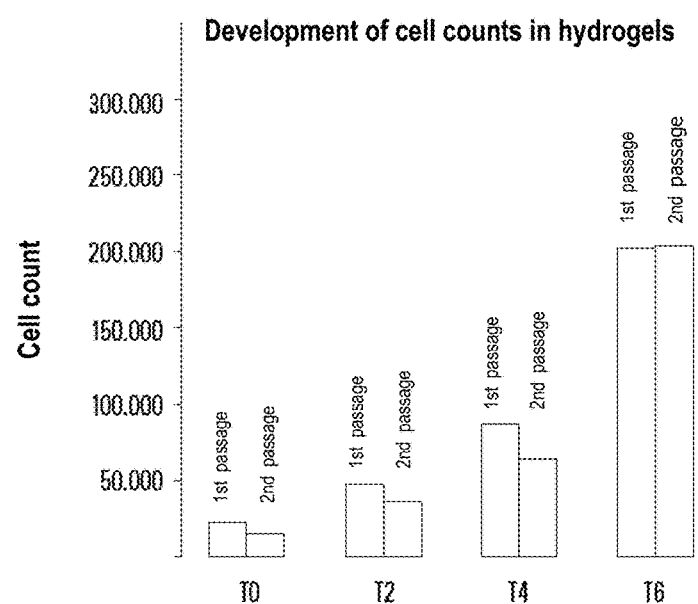
FIG. 2 shows, by way of example, the development of the cell counts during cultivation in hydrogel gel capsules.

FIG. 2 shows the development of the cell count in the hydrogel capsules produced as described above. The cells were encapsulated on day 0 (T0) and grew in the capsules up to day 7 (first passage, left-hand bars). Thereafter, the capsules were dissolved and the released cells encapsulated again and cultivated for a further 7 days (second passage, right-hand bars). A propagation by a factor of approx. 10 resulted for each passage/cycle. Propagation rates $>>10^3$ can be achieved by cyclical repetition of the process.

Figure 3:
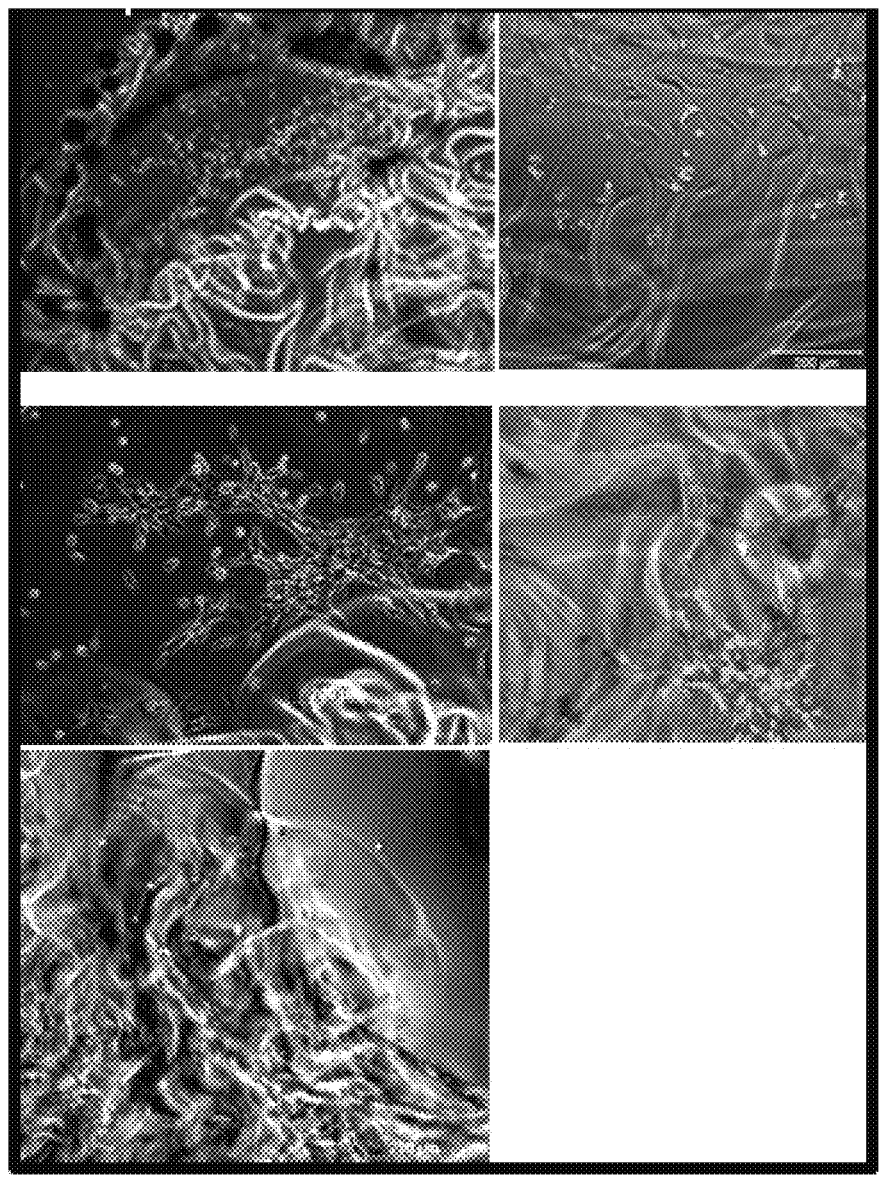
FIG. 3 shows cells/capsules in various stages of cultivation.

FIG. 3 shows cells/capsules in various states of cultivation.

The upper row shows the cells in the capsule shortly after encapsulation. To the left is a light microscope image, to the right a vital staining (nuclei: Hoechst, cell plasma: fluorescein diacetate).

The middle row shows the cells during expansion. On the right, in the vital staining, it can be clearly seen that the cells in the gel are adherent (extended morphology).

The lower image shows the process of capsule degradation and release of the cells.

The invention claimed is:

1. A method for cultivating cells in adhesion culture, comprising at least the following steps:
   a) dissolving or suspending a cross-linkable, biocompatible material with adhesion sites for cells in a cell culture medium,
   b) providing a cell suspension by suspending cells in the cell culture medium which contains the cross-linkable, biocompatible material, or in a medium which contains at least one component which is required to cross-link the cross-linkable, biocompatible material,
   c) introducing the cell suspension in drops into a medium under conditions which initiate or allow the cross-linking of the biocompatible material, wherein either the cell suspension or the medium, into which the cell suspension is introduced in drops, contains the cross-linkable, biocompatible material,
   d) forming stable capsules of cross-linked, biocompatible capsule material encapsulating adherent cells, wherein the adherent cells can grow in capsules,
   e) proliferating the adherent cells within the capsules for a defined time period,
   f) dissolving the capsule material by a physical or chemical stimulus and releasing the cells as a cell suspension,
   g) suspending the cells released in step f) in a cell culture medium, which contains a cross-linkable, biocompatible material, or in a medium which contains at least one component which is required to cross-link the cross-linkable, biocompatible material, and
   h) repeating steps c)-f) at least once thereby obtaining a suspension of cells.

2. The method according to claim 1, wherein step c) is carried out under conditions which support pore formation in the capsule material.

3. The method according to claim 2, wherein a gas is injected into the medium into which the cell suspension is introduced in drops or a gas-forming particulate material, which releases gas after exposure to a physical or chemical stimulus, is incorporated in the capsule material.

4. The method according to claim 1, wherein the conditions which initiate or allow the cross-linking of the biocompatible material in step c) encompass exposing the biocompatible material to a physical or chemical stimulus.

5. The method according to claim 4, wherein the physical or chemical stimulus in step c) is a member selected from the group consisting of a temperature change, a pressure change, ultrasound, electromagnetic radiation, a pH change, an action of enzymes, radical starters, addition of water, exclusion of water, and ions.

6. The method according to claim 5, wherein the physical stimulus in step c) is an ultrasound treatment of the biocompatible material and the chemical stimulus in step c) is a contact of the biocompatible material with a chemical agent selected from the group consisting of an enzyme and a bivalent cation, or comprises said contact.

7. The method according to claim 1, wherein the stimulus in step f) is a member selected from the group consisting of a temperature change, a pressure change, ultrasound, electromagnetic radiation, a pH change, an action of enzymes, complexing agents, solvents, and combinations thereof.

8. The method according to claim 7, wherein the stimulus in step f) comprises an action of proteases which are produced by the adherent cells themselves.

9. The method according to claim 1, wherein the cross-linkable biocompatible material comprises a material which is capable to form a hydrogel.

10. The method according to claim 9, wherein the hydrogel is a member selected from the group consisting of a protein-based hydrogel, a sugar-based hydrogel, a polyester hydrogel, a polyether hydrogel and a polyalcohol hydrogel.

11. The method according to claim 1, wherein the cross-linkable, biocompatible material was provided with adhesion sites for cells by a chemical coupling reaction.

12. The method according to claim 11, wherein the adhesion sites for cells comprise specific or non-specific adhesion or binding motifs for biological cells.

13. The method according to claim 1, wherein the capsules composed of cross-linked, biocompatible material comprise a material selected from a thermoresponsive material, a polyester, a polyether, a polyalcohol, silk, fibrin and a cross-linked alginate.

14. The method according to claim 11, wherein gelatin molecules are coupled to an alginate framework structure to provide an alginate-gelatin precursor material, and cross-linking of this alginate-gelatin precursor material is effected by contacting with a bivalent cation.

15. The method according to claim 1, wherein the capsules composed of cross-linked, biocompatible material further contain immobilized nutrients/growth hormones and/or reporter molecules.

16. The method according to claim 15, wherein the reporter molecules display a change of at least one parameter in the capsule, by a corresponding verifiable least one member selected from the group consisting of pH, viscosity, $CO_2$ concentration and $O_2$ concentration.

17. The method according to claim 15, wherein the reporter molecules are dyes or fluorescence markers.

18. The method according to claim 15, wherein the reporter molecules display a change of at least one parameter in the capsule, by a corresponding verifiable change in properties of the reporter molecules.

19. The method according to claim 18, wherein verifying the change of the parameter is effected by a spectroscopic or spectrometric method.

* * * * *